(12) United States Patent
Prieto-Dapena et al.

(10) Patent No.: US 6,759,570 B1
(45) Date of Patent: Jul. 6, 2004

(54) PROMOTER AND REGULATOR SEQUENCES *HA DS10 G1:* A GENE LEA OF SUNFLOWER EXPRESSED EXCLUSIVELY IN SEEDS FROM THE MATURATION PHASE

(75) Inventors: Maria Pilar Prieto-Dapena, Seville (ES); María Concepción Almoguera Antolinez, Seville (ES); Juán Bautista Jordano Fraga, Seville (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 09/600,848

(22) PCT Filed: Jan. 23, 1999

(86) PCT No.: PCT/ES99/00017

§ 371 (c)(1),
(2), (4) Date: Aug. 22, 2000

(87) PCT Pub. No.: WO99/37795

PCT Pub. Date: Jul. 29, 1999

(30) Foreign Application Priority Data

Jan. 23, 1998 (ES) .............................................. 9800122

(51) Int. Cl.[7] .......................... C12N 15/82; A01H 1/00; C07H 21/04
(52) U.S. Cl. .................. 800/278; 435/69.1; 435/820.1; 435/468; 435/410; 435/414; 435/415; 435/416; 536/23.1; 536/23.4; 536/23.6; 536/23.2; 536/24.1; 800/287; 800/288; 800/298; 800/312; 800/317.3; 800/320; 800/320.2; 800/322
(58) Field of Search ............................... 536/23.1, 23.4, 536/23.6, 23.2, 24.1; 435/69.1, 320.1, 468, 410, 414, 415, 416; 800/278, 287, 288, 298, 312, 317.3, 320, 320.2, 322

(56) References Cited

U.S. PATENT DOCUMENTS 5,929,304 A * 7/1999 Radin et al. ................. 800/288
5,952,490 A * 9/1999 Hanecak et al. ........... 536/24.5

OTHER PUBLICATIONS

Almoguera et al., Plant Mol. Biol., vol. 19, 1992, pp. 781–792.*

* cited by examiner

Primary Examiner—David Guzo
(74) Attorney, Agent, or Firm—Klauber & Jackson (57) ABSTRACT

The present invention refers to an isolated nucleic acid molecule for expression of a gene in seeds, having promoter activity, comprising a nucleotide sequence selected from the group consisting of SEQ ID NO:1, a first sequence at least 70% homologous to SEQ ID NO:1, with the functionality of SEQ ID NO:1, a second sequence at least 70% homologous to the sequence complementary to SEQ ID NO:1, with the functionality of SEQ ID NO:1, and fragments thereof, with the functionality of SEQ ID NO:1; to chimeric genes, constructs, vectors, expression cassettes, host cells and transgenic plants comprising said sequences; as well as to a method for expression of a gene specifically in seeds or seed parts using one of the mentioned sequences or chimeric genes comprising said sequence s and to a method for obtaining substances through the transferring of the mentioned chimeric genes to a plant and expressing said chimeric gene.

16 Claims, 5 Drawing Sheets

PROMOTER AND REGULATOR SEQUENCES HA DS10 G1: A GENE LEA OF SUNFLOWER EXPRESSED EXCLUSIVELY IN SEEDS FROM THE MATURATION PHASE

TECHNICAL SECTOR

Agriculture. The present invention refers to the obtaining of regulatory ("promoter") DNA sequences and the construction of new chimeric genes, and to the use of these sequences, capable of being specifically expressed in transgenic plant seeds. Ha ds10 G1 gene has the peculiarity of only being expressed in sunflower seeds from the maturation until the desiccation phase, without responding to hormones such as abscicic acid (ABA) or water stress in vegetative tissues. Furthermore, gene Ha ds10 G1 is expressed homogeneously in immature embryos and preferably in the palisade parenchyma of mature embryo cotyledons. These expression patterns, as well as the high activity levels of the gene, suggest that its regulatory sequences are particularly appropriate for the genetic manipulation of storage substances in seeds.

PRIOR ART

Up to now in order to confer specific expression in transgenic plant seeds, promoters have been isolated, characterised and used, especially belonging to plant genes which code for storage proteins or other products solely expressed in seeds, during different phases of development [see the following references and patents, as well as other documents cited therein Thomas T L, in *Plant Cell*, vol 5, pp 1401–1410, 1993; Gatehouse J A and Shirsat A H in *Control of Plant Gene Expression*, pp 357–375, CRC press, 1993; U.S. Pat. Nos. 5,530,192, 5,530,194 and 5,420,034]. For example, this has allowed the obtaining of new transgenic plants with modified fatty acid and storage protein content [see: Voelker T A, Worrell A C, Anderson L, Bleibaum 3, Fan C, Hawkins D J, Radke S E and Davies H M, in Science, vol. 257, pp.72–74, 1992; and Saalbach I, Pickardt T, Machemehl F, Saalbach G, Schieder O, and Muntz K, in *Molecular and General Genetics* 242: 226–236, 1994]. Other promoters with different tissue specificity in seed and varied temporal expression patterns could be useful for the development of the enormous potential of this technique. Recently the expression in seeds of genes that code for low molecular weight heat shock proteins was described (sHSPs: small heat-shock proteins). One of these genes, Ha hsp17.7 G4, shows in tobacco transgenic plants, expression patterns appropriate for its possible use in the genetically engineered modification of seeds: this gene is expressed from early seed maturation phases, and is specific of cotyledon tissue [Coca M A, Almoguera C, Thomas T L and Jordano J, in: *Plant Molecular Biology* 31: 863–876, 1996]. However, gene Ha hsp17.7 G4, like other sHSP plant genes expressed in seeds, is also expressed in response to heat (heat shock) in plant vegetative tissues after seed germination. The latter makes its use in genetic engineering impossible in the case that regulatory DNA sequences that guarantee the absence of expression of chimeric genes outside of the seed are required: for example, when the expression elsewhere of these genes may affect the viability, the growth, or the health of the transgenic plants. To solve these problems the Ha hsp17.7 G4 gene regulatory sequences were modified in such a way that the chimeric genes containing these sequences maintain their expression in seeds, and lose their heat induction; a procedure which can be used for the modification and similar use of regulatory sequences of other sHSP genes expressed in seed [Almoguera, Prieto-Dapena and Jordano, patent request #9602746 (Spanish Patent Office)]. Alternatively, a similar use for the promoter and regulatory sequences of the sunflower gene Ha hsp17.6 G1, which is only expressed in seeds, is proposed. This gene does not respond to heat or other types of stress (cold, dehydration, ABA hormone treatment) in vegetative tissues [Carranco, Almoguera and Jordano, Spanish patent application #970121.

Alternative analogous uses for promoter and regulatory sequences of sunflower LEA Ha ds10 G1 gene are proposed. Gene Ha ds10 G1 has been found in a genomic clone corresponding to a previously described cDNA (Ha ds10, access number X506999) whose expression patterns were not totally known [Almoguera and Jordano, *Plant Mol. Biol.* 19:781–792, 1992]. The promoter and regulatory sequences of this gene (Ha ds10 G1) have been cloned and are described, characterised and used for the first time in the examples of this application. The Ha ds10 G1 gene belongs to the Class I LEA (Late Embryogenesis Abundant) gene family (D-19 or LEA-I type ) These genes code for highly conserved proteins in various plant species, and their expression is usually restricted to seeds and early germination phases [see for example the following reviews: Dure III, L., Structural motifs in Lea proteins, in *Plant Responses to Plant Dehydration During Environmental Stress.*, Close T J and Bray E A Eds., *Current Topics in Plant Physiology* 10: 91–103, 1993; and Delseny M, Gaubier P, Hull G. Saez-Vasquez J, Gallois P, Raynal M, Cooke R, Grellet F., *Nuclear Genes expressed during seed desiccation: relationship with responses to stress*, in Stress-induced Gene Expression in Plants (Basra, A. S., ed.), pp. 25–59, Harwood Academic Publishers, Reading, 1994]. LEA gene promoters have not been considered so good candidates for their use in seed storage substance modification projects, since usually their activity is expressed in later seed maturation phases, such as embryo desiccation [Kridls J C, Knauf V C, Thompson G a in *Control of Plant Gene Expression*. pp. 481–498, CRC press, 1993]. However, LEA genes that are activated in maturation phases prior to desiccation are known, such as the cotton genes denominated LEA-A [Hughes D W and Galau G A, *The Plant Cell* 3:605–618, 1991]. Examples of activation prior to desiccation are also known in the class I LEA genes, such as in the case of At Em1, emb564 and emb1 genes [in arabidopsis, maize and carrot, respectively: Gaubier P, Raynal M, Hull G, Huestis G M, Grellet F, Arenas C, Pages M, and Delseny M, *Mol. Gen. Genet.*, 238: 409–418, 1993; Williams B, and Tsang A, *Plant Mol. Biol.*, 16: 919–923, 1991; Wurtele E S, Wang H, Durgerian S, Nikolau B J, and Ulrich T H. *Plant Physiol.* 102:303–312, 1993]. These examples seem to indicate the possible use of regulatory sequences from genes of this family, for the modification of seeds. However, its specific use would be limited both by the expression levels obtained in each case and in each development phase; as well as by the different tissue specificity. Thus, even though in Arabidopsis the At Em1 gene is early activated, its expression is basically restricted to cotyledon provascular tissue and cortical tissue external to the embryonic axis [Gaubier, P., Raynal, M., Hull, G., Huestis, G M., Grellet, F., Arenas, C., Pages, M., and Delseny, M., *Mol. Gen. Genet.*, 238: 409–418, 1993]. In the case of the carrot gene, emb1, its mRNA are preferably localised in the embryonic meristems, especially in the procambium [Wurtele E S, Wang H, Durgerian S, Nikolau B J, and Lylrich T H. *Plant Physiol.* 102:303–312, 1993]. No gene sequence of the emb564 gene has been published and the exact localisation of its mRNA is unknown [Williams B and Tsang A, *Plant Mol. Biol.*, 16: 919–923, 1991].

The expression of sunflower gene Ha ds10 G1, as well as its promoter and regulatory sequences present unique characteristics among the other members of the LEA-I family, as described below, which means that these sequences may be potentially used for the modification of seeds by genetic engineering.

DESCRIPTION OF THE INVENTION

The present invention refers to the isolation and characterisation of the promoter and regulatory sequences of a sunflower LEA-I gene, Ha ds10 G1, in transgenic tobacco plants. These sequences (Example 1) present highly appropriate characteristics for their use in the modification of seeds (e.g. storage substances). The advantages of their possible use in transgenic plants are demonstrated in other examples: A. Studies of HA ds10 mRNA accumulation and localisation in the homologous system (Example 2). These studies demonstrate both the high expression levels reached during embryogenesis since early maturation phases, as well as the absolute seed specific localisation, accompanied of a homogenous distribution in embryos, which terminates essentially restricted to the cotyledon palisade parenchyma, a tissue specialised in the accumulation of sunflower storage substances. B. In example 3 the possible use of such sequences, via the construction and analysis of various chimeric genes in transgenic plants, is illustrated, using the promoter and combinations of various Ha ds10 G1 regulatory sequences (5'-flanking, coding, intron and 3'-flanking), with the reporter gene of bacterial β-glucuronidase (GUS). These examples demonstrate the usefulness of the different chimeric genes tested in a heterologous model (tobacco): high expression level and seed specificity since early maturation phases, as well as the functional contribution of the various sequences tested. The examples attached demonstrate that the seed specificity is basically conferred by the promoter and the 5'-flanking sequences of Ha ds10G1 (including untranscribed and transcribed sequences, such as the 5'-UTR, and part of the coding sequence). Additionally, the 3'-flanking sequences increase expression levels in seeds, and the intron specifically reduces the expression levels in non-embryonic tissues. Due to the conservation of the regulation of embryonic gene expression in plant seeds, including LEA-I genes [Thomas T L, in I 5:1401–1410, 1993]; these sequences could be used both in the homologous system (sunflower) as in other heterologous systems of great economic importance (for example oilseed rape, soybean, maize, etc).

The practical embodiment of this invention, represented by the attached examples and figures, uses conventional Molecular Biology, Microbiology, recombinant DNA and transgenic plant production techniques that are common practice in laboratories specialised in these fields. These techniques have been explained in sufficient detail in the scientific literature [Sambrok J, Fritsch E F, and Maniatis T, *Molecular Cloning: A Laboratory Manual*, Cold Spring Harbor laboratory Press, 2nd Edition, 1989; Glover D M, *DNA Cloning*, IRL Press, 1985; Lindsey K., *Plant Tissue Culture Manual*, Kluwer Academic Publishers, 1993; and Gelvin S B, Schilperoort R A, Verma D P S, *Plant Molecular Biology Manual*, Kluwer Academic Publishers, 1992]. For more details, other references are cited in the corresponding section in this application.

EXAMPLE 1

Figure 1:
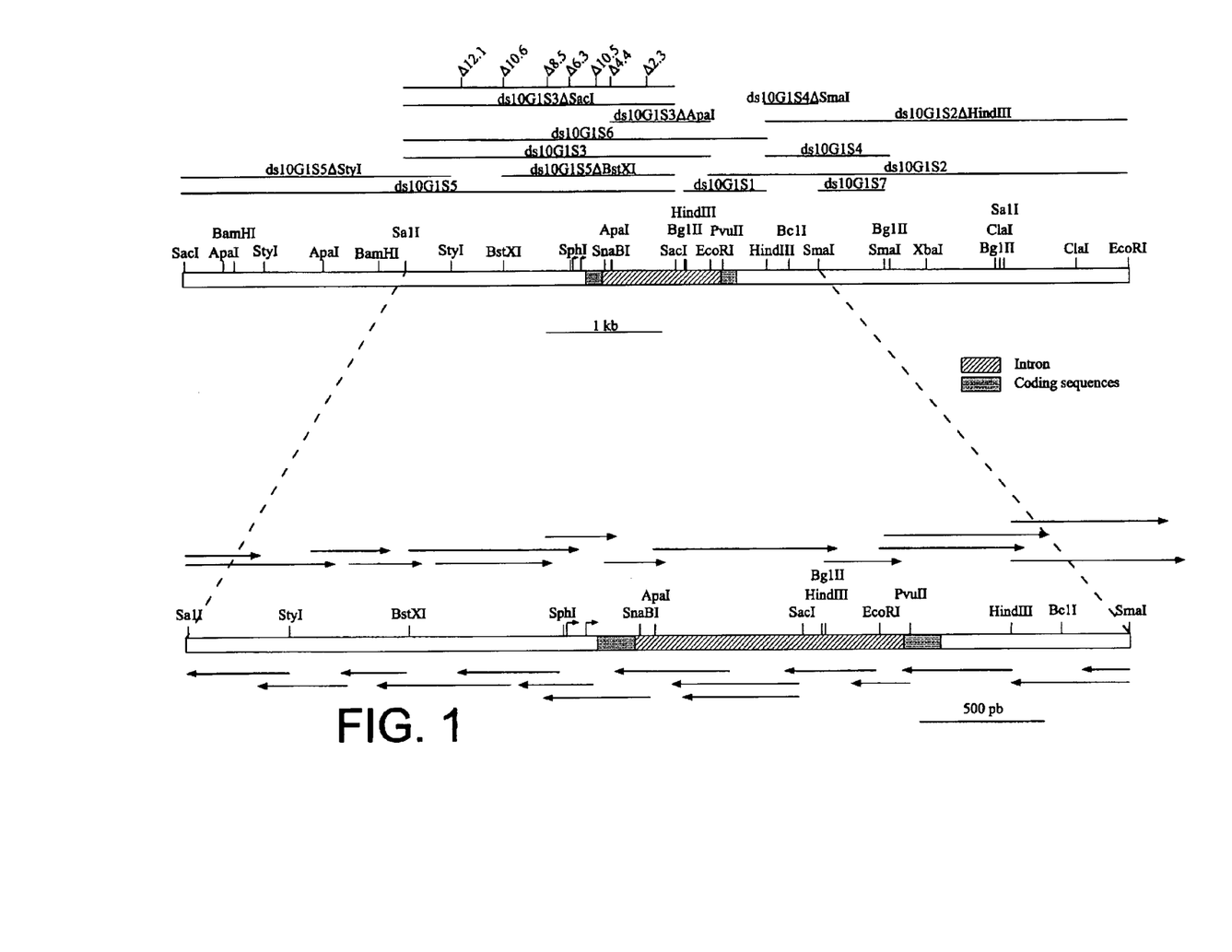

Cloning, Determination of Restriction Map, Nucleotide Sequence and Analysis of the Ha ds10 G1 Promoter To obtain the Ha ds10 G1 clone, the sunflower genomic DNA gene library described by Coca et al. [*Plant Mol. Biol.* 31: 863–876, 1996] was screened, with the probe corresponding to total Ha ds10 cDNA [Almoguera and Jordano, Plant Mol. Biol. 19: 781–792, 1992]; using standard hybridisation conditions and molecular cloning procedures described in detail in the first reference of Coca et al., 1996. A phage (IGEM11) with a sunflower genonic DNA insert of approximately 16.5 Kb—whose partial map is shown in FIG. 1—was isolated. Using restriction analysis it was determined that the two fragments adjacent to the Sac I site (4.2 and 9.3 Kb) contain the sequences that hybridise with the cDNA. A detailed restriction map of the first of these fragments was determined and part (4 Kb) of the second (FIG. 1). Different genomic DNA subfragments, corresponding to the mapped region, were cloned in pBluescript SK+ vector, resulting in plasmids whose names and inserts are listed in FIG. 1. The 3617 bp nucleotide sequence between the Sac I and Sma I sites (FIG. 1, lower section) was determined from these plasmids on both DNA strands using the Sanger (dideoxy) method. These data are presented in SEQ No. 1. By comparing the sequences it was confirmed that part of the genomic sequence determined corresponds to Ha ds10 cDNA [Almoguera and Jordano, *Plant Mol. Biol.* 19: 781–792, 1992, GenBank access number X59699]. The amino acid sequence of the protein coded by the Ha ds10 G1 gene is indicated below the corresponding nucleotide sequences. In the genornic DNA, the coding region is interrupted by an abnormally long intron (1024 bp), even though it is situated in a conserved position in other class I LEA genes (see data reviewed by Simpson G C, Leader D J, Brown J W S and Franklin T, in *Characteristics of Plant pre-mRNA Introns and Transposable Elements, Plant Mol. Biol.* LabFax, pp 183–252; Croy RRD Ed., Bios Scientific Publishers Ltd. 1993). The only difference between the gene sequences coding for mRNA and those of cDNA, was a two nucleotide inversion (GC instead of CG) within the second exon (in positions +1176 and +1177 from the initiation codon). Said inversion induces an amino acid change (S instead of T) in the protein sequence. The difference is due to an error (a compression) in the initial reading of the cDNA sequence reactions. The Ha ds10 G1 sequences determined also include 1576 bp of the gene promoter and 5'-flanking region, as well as the 553 bp of 3'-flanking genomic regions which are not present in the original cDNA.

Figure 3:
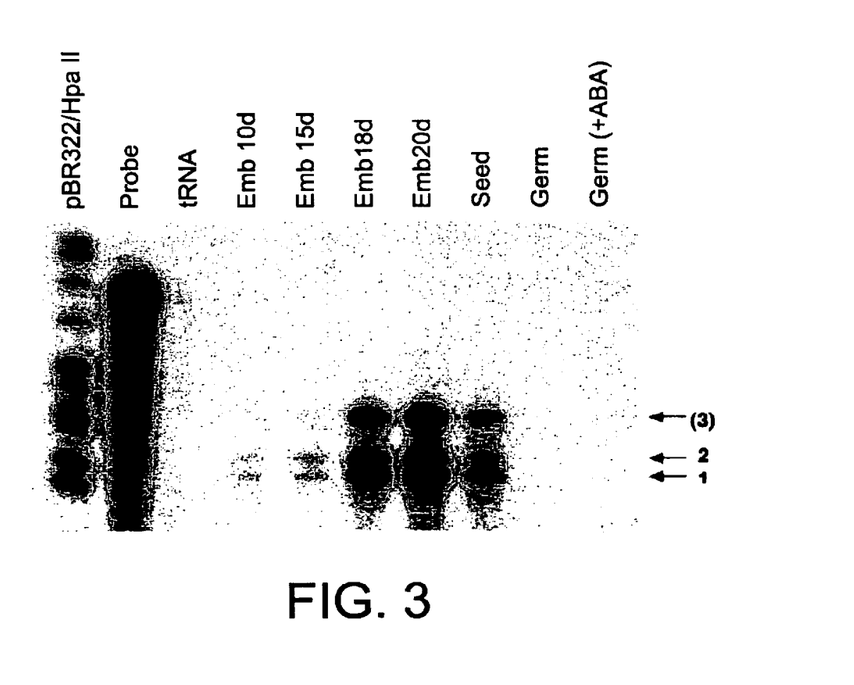

Three possible transcription initiation sites were determined in the Ha ds10 G1 promoter by the primer extension technique. Two of these sites have been confirmed with other techniques (sites 1 and 2, indicated by arrows in SEQ No. 1). For this purpose the procedure described by Domon et al. was used [Domon C, Evrard J L, Pillay D T N and Steinmetz A. *Mol. Gen. Genet.* 229:238–244, 1991], whereby the total sunflower embryo RNA was hybridised with the synthetic primer 5'-CTCCTGTTCCGGAATTTTGCGTGT-3' [SEQ ID NO: 2]. The sequence of said synthetic primer corresponds to that of the non coding strand of Ha ds10 G1, between positions +25 and +48, from the initiation codon. The hybridisations with the primer were carried out at 62° C. The hybrids were extended with AMV reverse transcriptase, for 90 min at 42° C. The extension products were analysed on 6% PAGE sequencing gels, along with sequence reactions produced using the same primer. Initiation sites 1 and 2 (at positions −33 and −25, see SEQ No. 1) are functional, and are detected independently using the ribonuclease A protection technique (RNAse A, see FIG. 3A). A third initiation site (site 3, in position −119 in SEQ No. 1) could not clearly be confirmed with this technique. These initiation sites functionally define the 3' end of the Ha ds10 G1 gene promoter.

The analysis of the proximal sequences of the Ha ds10 G1 gene promoter demonstrated that the two initiation sites detected (sites 1 and 2) are found at an appropriate distance from a possible TATA sequence (at position −86). The possible more distal site (site 3, −119) does not have clear TATA sequences in its proximity. Apart from these promoter elements, two possible RY "boxes" (RY1 and RY2 at positions −129 and −65 of SEQ No. 1) were observed, analogous to those that participate in the regulation of the expression of numerous plant genes in seeds [Dickinson D C, Evan R P, and Nielsen R C, in *Nucleic Acids Research* 16: 371, 1988].

Figure 2:
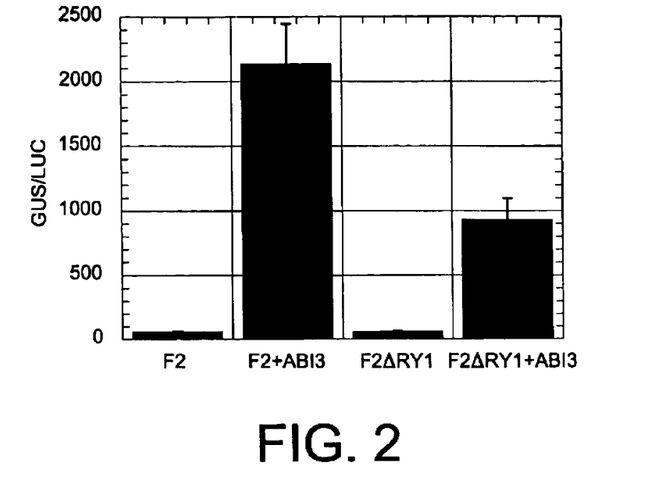

The RY1 box sited at position −129 was modified by verifying through transient expression experiments in sunflower embryos, its functional requirement for the trans-activation of the Ha ds10 G1 promoter by ABI3 type transcription factors [Giraudat J., Hauge B M, Valon C, Smalle J, Parcy F, Goodman H M in *The Plant Cell*: 1251–1261, 1992]. In order to do this, modifications of the ds10::GUS fusions constructed for transgenic plant studies were prepared (see Example 6.3 and FIG. 5). The chimeric genes contained in these two fusions (ds10F1 and ds10F2) were purified as DNA fragments, which were subcloned by ligation into pBluescript SK+ (Promega) vector, thus replacing the binary vector sequences by smaller ones. Smaller binary vector sequences are more useful for transient expression experiments. The plasmid pSKds10F1 was obtained by using the Sal I-Eco RI fragment (with the chimeric gene obtained from ds10F1). In the case of ds10F2, the Sph I-Eco RI fragment (from position −125 in Ha ds10G1, to the 3' end of nos) was ligated to the complementary fragment (which contains the promoter and 5'-flanking sequences of Ha ds10 G1), purified after digestion of pSKds10F1 with Sph I and Eco RI, resulting in the pSKds10F2 plasmid. Finally, from the pSKds10F1 and pSKds10F2 plasmids (maps not shown) mutagenised versions were obtained by digestion of their DNA with Sph I, blunting the resulting ends by treatment with T4 DNA polymerase, followed by re-ligation of the DNA. Plasmids pSKds10F1ΔRY and pSKds10F2ΔRY (maps not shown) were obtained. These plasmids only differ by a 5 nucleotide deletion between positions −126 and −122 of the Ha ds10 G1 promoter. These changes destroyed the RY1 box present in the ds10F1 and ds10F2 chimeric genes (see FIGS. 1, 2 and 5), this was verified by the Sanger (dideoxy) method sequencing reactions, using the primer 5'CTCCTGTTCCGGAATTTTGCGTGT3' [SEQ ID NO: 2] (non coding strand of Ha ds10G1 between positions +25 and +48).

The trans-activation experiments in transient expression were carried out by bombarding sunflower embryos with projectiles coated with DNA mixtures from different plasmids. These mixtures contain the reference plasmid pD0432 [Ow D W, Wood K V, deLuca M, de Wet J R, Helinski D and Howell S H. Science 234: 856–859, 1996], with the firefly (*Photinus pyralis*) luciferase (LUC) gene regulated by the CaMV 35S promoter, the fusion of ds10::GUS tested in each case (with intact or modified RY1 sequences), and an effector plasmid, pABI3, which expresses the ABI3 factor under control of the CaMV 35S promoter. pABI3 was obtained by substituting the Pv ALF cDNA from the pALF plasmid [Bobb A J, Eiben H G, an Bustos M M in *The Plant Journal* 8: 331–343, 1995], with ABI3 cDNA. The ABI3 cDNA was cloned as an Xba I fragment (blunted with Klenow enzyme)-Eco RI (partial), fragment purified from the pcabi3-4F plasmid [Giraudat J., Hauge B M, Valon C, Smalle J, Parcy F, Goodman H M in *The Plant Cell* 4: 1251–1261, 1992]. pABI3 plasmid is added to, or omitted from, the mixture to test the effect of the ABI3 factor on GUS expression in the fusion tested. The experiments were essentially carried out as described by Bobb et al., [Bobb A J, Eiben H G, and Bustos M M in *The Plant Journal* 8: 331–343, 1995], with the following modifications: Sunflower embryos (17–20 dpa) were prepared as follows: Sunflower seeds were sterilised by washing in 70% ethanol for 1 min, and in 2% sodium hypochlorite with a drop of Triton X-100 for 40 min, finally rinsed several times with distilled water, and then peeled under sterile conditions. The embryos are cut longitudinally (separating the two cotyledons) and placed, with the cut surface down on MS solid medium plates, containing 2% sucrose and 0.5 M sorbitol. They are then pre-cultured for 2–4 h in the dark, at room temperature (25° C.). All the plasmids were purified using the Quantum midiprep kit (Biorad). Normally for each bombardment 0.2 μg of reference plasmid, 0.1 μg ds10::GUS plasmid, and 1 μg of effector plasmid (or the same amount of pJIT82 plasmid in the negative controls) were used. For the preparation of the gold particles, as well as the DNA precipitation onto them, the method described by Chem et al. was followed [Chern M S, Bobb A J and Bustos M. *The Plant Cell* 8: 305–321, 1996]. The particle bombardment was carried out using the Biolistic PDS-1000 He system (Biorad). The bombardment conditions were the following: 1550 psi rupture membrane, 1.6 μm diameter gold particles, distance from rupture membrane to macrocarrier was 8 mm, distance from macrocarrier to grid was 6 mm, and the distance to the tissue to be bombarded was 6 cm. The bombarded cotyledons were incubated for 24 h at 28° C. in the dark, after bombardment, the GUS activity (relative to LUC activity) was tested as described by Bobb et al. [Bobb A J, Eiben H G, and Bustos M M in *The Plant Journal* 8: 331–343, 1995].

The addition of pABI3 effector plasmid had a clear effect on the relative expression of GUS/LUC in bombardments with the pSKds10F2 fusion (average increase in relative activity ≈46.2X). On the other hand, if the trans-activation was carried out with the same plasmid with a mutation in the RY box (pSKds10F2ΔRY1), a significant reduction in the average increase in relative activity, due to the ABI3 effect (≈26.3X), was observed. This result, shown in FIG. 2, confirms the functional requirement of the RY1 sequence (position −129 in SEQ No. 1). Therefore, this RY box participates in the transcriptional activation in seeds of the Ha ds10 G1 promoter for ABI3 type factors [Giraudat J., Hauge B M, Valon C, Smalle J, Parcy F, Goodman H M in *The Plant Cell* 4: 1251–1261, 1992]. Other promoter sequences (e.g. RY2 in −65) could also contribute to the transactivation effect observed, since the mutation tested does not completely destroy the activator effect of ABI3.

EXAMPLE 2

Accumulation and Specific Localisation of Ha ds10 mRNA in Sunflower Embryos

The messenger RNA accumulation patterns of the Ha ds10G1 gene were determined by the Ribonuclease A (RNAse) protection technique, described in detail by Almoguera et al. [Almoguera C, Coca M A, Jordano J. *Plant Physiol.* 107: 765–773, 1995]. To do this, total RNA samples prepared from seed embryos at different stages of development, under normal growth conditions, were used [Almoguera and Jordano, *Plant Mol. Biol.* 19: 781–792, 1992; Coca et al., *Plant Mol. Biol.* 25: 479–492, 1994]; from 3-day seedlings after imbibition (dpi); and from different adult plant organs before flowering. The seedling and plant RNA were prepared from plant material obtained both under controlled growth conditions [Almoguera and Jordano, *Plant Mol. Biol.* 19: 781–792, 1992; Coca M A, Almoguera C, and Jordano J. *Plant Mol. Biol.* 25: 479–492, 1994; Coca M A, Almoguera C, Thomas T L, and Jordano J. *Plant Mol. Biol.* 31: 863–876, 1996], and after stress treatments. Said stress treatments can be water deficit [Almoguera C, Coca M A, and Jordano J. *Plant J.* 4: 947–958, 1993; Coca M A, Almoguera C, Thomas T L, and Jordano J. *Plant Mol. Biol.* 31:863–876, 1996]; or after addition of hormones such as absicic acid [Almoguera C and Jordano J. *Plant Mol. Biol.* 19: 781–792, 1992; Coca M A, Almoguera C, Thomas T L, and Jordano J. *Plant Mol. Biol.* 31: 863–876, 1996]. The conditions used in each treatment are described in detail in the references cited for each case. The riboprobe used to detect the Ha ds10 G1 mRNA is 396 nucleotide long. 63 of these 396 nucleotides are sequences of the pBluescript SK+ vector. The remaining nucleotides are the sequence of the non coding strand of Ha ds10 G1 between positions +212 and −121 (Sph I). This hybrid probe with the 5' end of Ha ds10 G1 messenger RNAs, exceeding the more distal transcription initiation site (site 3, SEQ No. 1), allows the detection of messenger RNA (mRNA) produced from the three initiation sites and the experimental verification of the initiation positions. This riboprobe was prepared by in vitro transcription, using RNA polymerase T3 and ds10G1S3Δ4.4 plasmid DNA (FIG. 1) as a template, which contains the Ha ds10G1 sequences between −1576 (Sal I) and +212 cloned in the pBluescript SK+ vector.

FIG. 3 shows that the Ha ds10 G1 messenger RNAs are only detected in seeds. Higher accumulation levels are observed around 18–20 dpa. Gene expression is detected from 10 dpa and it disappears after germination (FIG. 3). Treatments with ABA, or water deficit did not induce the accumulation of Ha ds10 G1 messenger RNAs (data shown for ABA in seedlings, FIG. 3). As a positive control in the RNA samples tested for the different treatments, hybridizations (data not shown) with another previously described 651 nucleotide riboprobe of Ha hsp17.7 G4 gene were carried out [Coca et al., *Plant Mol. Biol.* 31: 863–876, 1996]; since this gene is expressed in response to the different treatments tested. These analysis showed that the Ha ds10 G1 mRNAs were only accumulated in seeds, under normal growth conditions and since early stages of maturation, confirming the initiation from at least sites 1 and 2 (indicated in SEQ No. 1). The band marked with number 3 (FIG. 3) does not coincide well with the expected size for initiation site 3 (SEQ No. 1). This band could be due to the protection of messenger RNA sequences of a highly homologous gene, or even Ha ds10 G1 itself, containing intron sequences (unprocessed mRNA).

The distribution of Ha ds10 G1 mRNAs in sunflower embryos was investigated by in situ hybridisation localisation experiments. In order to do this, embryos were embedded in paraffin, fixed, sectioned and hybridised with specific probes; essentially as described by Molinier [in the thesis: *Diplome d'Etudes Approfondies de Biologie Cellulaire et Moléculaire*, Universite Louis Pasteur, Strasbourg, 1995]. The fixing time was increased from 16 h at 4° C. to 5 days, the increase depending on the age of the embryos. The dehydration of the fixed embryos was carried out by successive incubations (2 times each for 30–90 min.) in 10%, 20%, 30%, 40%, 60%, 70%, 95% and 100% ethanol; followed by immersion in 100% toluene (1–3h, 2 times). The fixed embryos were first embedded in toluene : paraffin (1:1), at 65° C. for 6–15 h, followed by 5 consecutive inclusions in paraffin, at 60° C. for 5–15 h. The pre-hybridisations and hybridisations with the probes were carried out at 45° C. The specific Ha ds10 G1 riboprobe, corresponding to the mRNA 3' end was prepared as follows: The ds10G1S1 plasmid (FIG. 1) was used as a template to prepare two in vitro transcription probes [Almoguera C, Coca M A and Jordano J. *Plant Physiol.* 107: 765–773, 1995] marked with DIG-UTP. The ds10-3' (−) is obtained by digesting plasmid DNA with Pvu II and carrying out the transcription with RNA polymerase T3. This probe corresponds to the non-coding strand of Ha ds10 G1 between positions +1202 (Pvu II in the second exon) and +1592 (3' end). The second probe [ds10-3' (+), used as a control], was prepared digesting Ha ds10 G1S1 DNA with Bam HI (in the polylinker); and carrying out the transcription with RNA polymerase T7. Probe ds10-3' (+) contains the coding chain of Ha ds10 G1, between position +870 and +1592. The specificity of the hybridisation was determined by Southern blot experiments similar to those described by Almoguera and Jordano [*Plant Mol. Biol.* 19: 781–792, 1992]. While the hybridisation with a total cDNA probe detects bands corresponding to some 4–5 different genes in the sunflower genome [Almoguera C, and Jordano J. *Plant Mol. Biol.* 19: 781–792, 1992], a single gene (with a slight cross hybridisation with another one, data not shown) was detected using probe ds10–3'(−).

Figure 4:
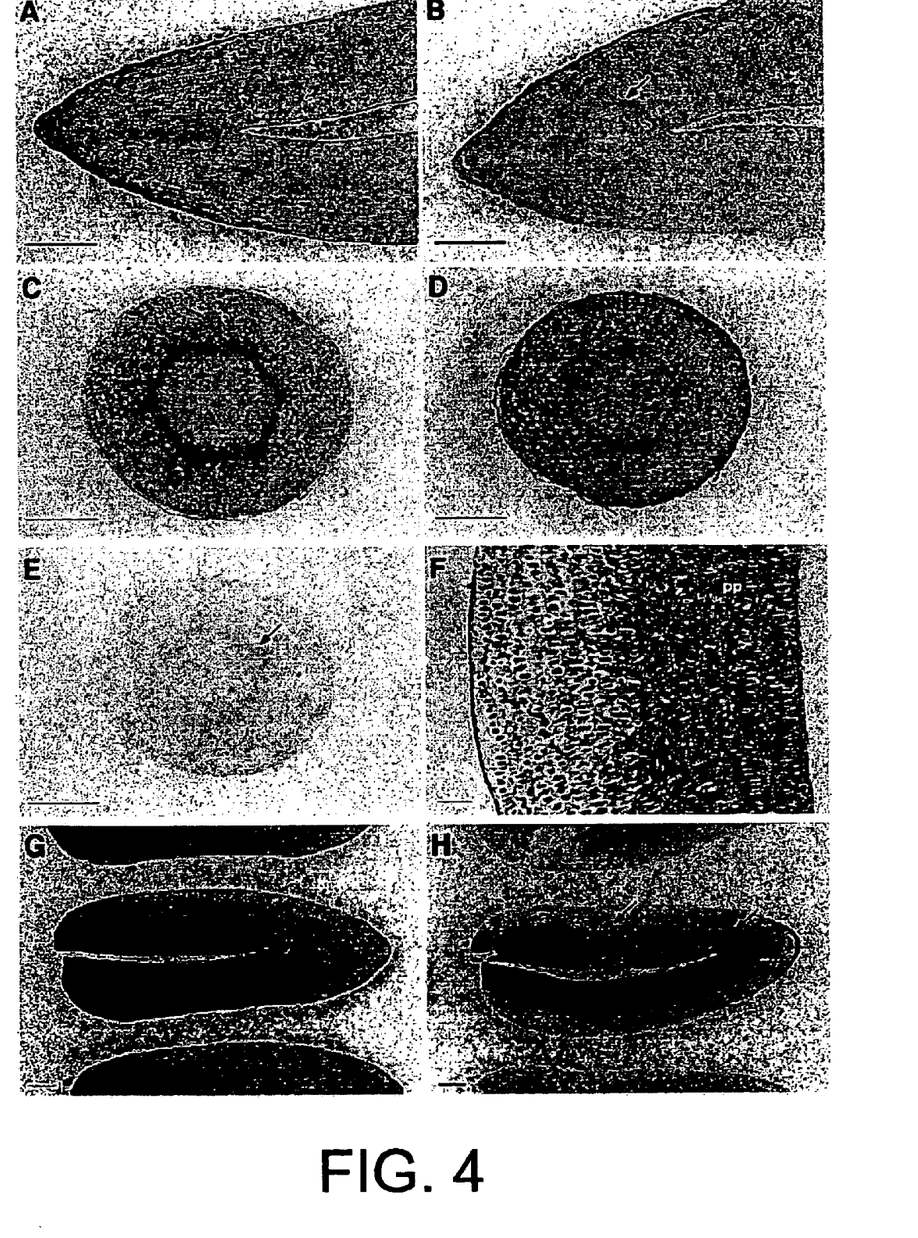

The results obtained in the RNA localisation experiments are shown in FIG. 4. Probe ds10-3'(−) is complementary to Ha ds10 G1 mRNA, and has opposite polarity to Ha ds10 G1 mRNA, what allows its detection. The results obtained agree with the protection data shown in FIG. 3, and demonstrate its accumulation in embryos from 12–15 dpa (FIG. 4A) to 21–28 dpa (FIGS. 4C, F and H). This accumulation takes place to high levels, which can be deduced from the short time required for its histochemical detection (2–4 hours). In immature embryos (FIG. 4A) the distribution of Ha ds10 G1 mRNA is homogeneous and comparable (FIG. 4B) to that of 18S rRNA, which is detected using another riboprobe corresponding to fragment G (Eco RI) of the radish 18S gene [described by Delcasso-Tremousaygue D, Grellet F, Panabieres F, Ananiev E D, and Delseny, M. in *Eur. J. Biochem.* 172: 767–776, 1988]. In more mature embryos (21 dpa, FIG. 4C) the Ha ds10 G1 mRNA are also localised fairly homogeneously, with a more intense accumulation detected in the vascular bundles (procambium), something which is neither observed with the 18S rRNA probe nor in this or other development stages (FIGS. 4D, B and G). Finally, at 28 dpa the Ha ds10 G1 mRNA are preferably localised in the palisade parenchyma, a tissue specialised in the accumulation of storage substances, located in the internal face of cotyledons (FIGS. 4F and H). The localisations with probe ds10-3' (+), with the same polarity as the Ha ds10 G1 mRNA, did not give any hybridisation signal, which was a control for the previously described experiments (compare FIGS. 4C and E). These experiments demonstrated that the Ha ds10 G1 mRNA expression patterns in sunflower are very special. The expression observed in seeds, with high levels of accumulation since early embryonic maturation stages (10–12 dpa), are combined with spatial distributions which change from homogeneity to a greater abundance in storage substance deposit tissues (palisade parenchyma). The distribution and accumulation pattern of Ha ds10 G1 mRNA is different from that presented by other plant genes belonging to the same family [Wurtele E S, Wang H Q, Durgerian S, Nikolau B J and Ulrich T H. *Plant Physiol.* 102: 303–312, 1993; Gaubier, P., Raynal, M., Hull, G., Huestis, G M., Grellet, F., Arenas, C., Pages, M., and Delseny, M., *Mol. Gen. Genet.*, 238: 409418, 1993]. These results indicate the potential usefulness of chimeric genes that incorporate Ha ds10 G1 regulatory sequences for the modification of seeds by genetic engineering.

EXAMPLE 3

Construction of ds10G1::GUS Chimeric Genes and Their Analysis in Tobacco Transgenic Plants As an example of the possible uses of the promoter and the regulatory sequences of Ha ds10 G1 gene in the construction of chimeric genes with specific expression in transgenic plant seeds, the construction and analysis of 4 ds10G1::GUS translational fusions in tobacco transgenic plants (FIG. 5) are described below. These fusions contain the promoter and different combinations of flanking and intragenic sequences of Ha ds10 G1 gene for its functional analysis. These 4 fusions provide high levels of expression of the reporter gene (GUS) in seeds from early maturation stages (FIG. 6), confirming the observations in the homologous system (Example 2, FIGS. 1–4).

Figure 5:
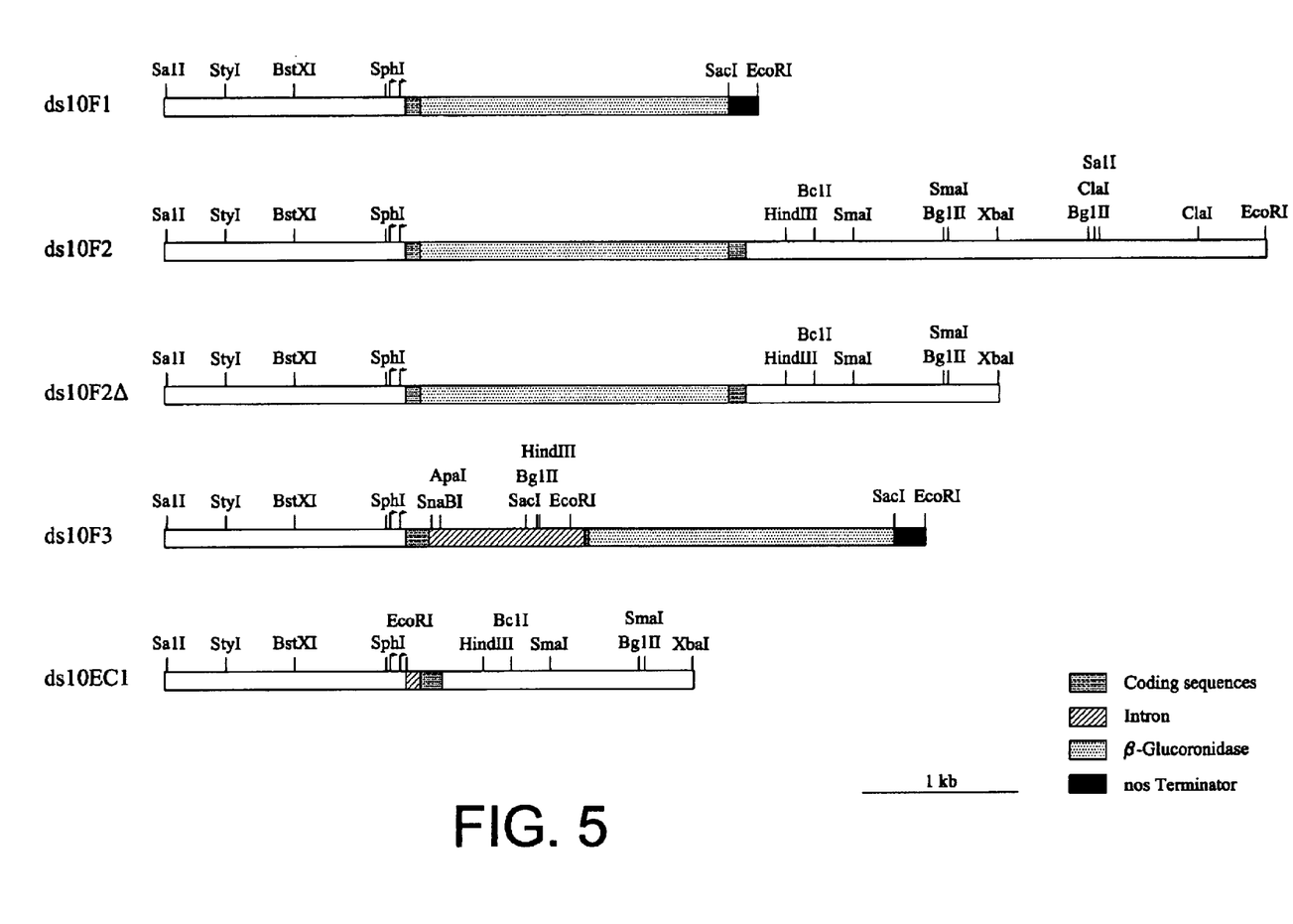
FIG. 5. Restriction maps of ds10::GUS fusions and optimised expression ds10 EC1 cassette, constructed in Examples 3 and 4. The Ha ds10 G1 and other genes contained in each case are shown by shading of varying intensity. The transcription initiation sites from the Ha ds10 G1 promoter are marked with arrows.

The first of these constructions, ds10F1 (FIG. 5) was obtained from the ds10G1S3 plasmid (FIG. 1), which contains the genomic sequences of Ha ds10 G1 between Sal I (−1576) and Eco RI (+1086), subcloned into the corresponding restriction sites of the pBluescript SK+ vector (Promega). The Ha ds10 G1 sequences between Eco RI (+1086) and position +98 (in the first exon) were deleted by treating with Exonuclease III of the ds10G1S3 DNA (previously digested with Hind m and Pst 1) Said deletion results in the ds10G1S3Δ10.5 plasmid (FIG. 1). This plasmid was digested with Barn H1 (polylinker restriction target situated immediately adjacent to position +98 of Ha ds10 G1), and then, filling in the digested DNA ends using the Klenow fragment of DNA polymerase 1. The DNA was then digested with Sal I, and the 1679 bp fragment containing the Ha ds10 G1 sequences between Sal I (−1576) and the filled end of Bam HI was purified. This fragment was cloned between the Sal I and Sma I sites of the pBI 101.2 binary vector, resulting in ds10F1. ds10F1 is a translational fusion which contains 1576 nucleotides of 5'-flanking Ha ds10 G1 sequences (from ATG) and the first 98 nucleotides of the coding gene, in phase with the GUS gene (FIG. 5). The ds10F2 fusion was derived from ds10F1, through the insertion of a genomic DNA fragment of Ha ds10 G1 comprised between positions (FIG. 1) +1205 (Pvu II) and Eco RI (=+4670). This fragment contains part of the second exon and −3370 nucleotides of 3'-flanking sequences (from the termination codon in position +1301); and replaces the nos-3' sequences in the ds10F1 fusion. The Pvu II-Eco RI insert was purified from ds10G1S2 plasmid DNA. For the insertion of this fragment, the ds10F1 DNA was digested with Sac I, and the DNA ends were blunted by treating with T4 DNA polymerase I. Then, the DNA thus treated was digested with Eco RI, and the fragment including the Ha ds10 G1 sequences was purified. This fragment was ligated to the previously described Pvu II-Eco RI insert (with the Ha ds10 G1 3'-flanking sequences), resulting in the ds10F2 fusion (FIG. 4). The ds10F2Δ fusion (FIG. 4) was obtained from ds10F2, through the deletion of the Ha ds10G1 3'-flanking sequences between Xba I (=+2830) and Eco RI (=+4670). To do this, ds10F2 DNA was digested with both enzymes, religating, after blunting the resulting DNA ends with the Klenow fragment of DNA polymerase I. Finally, the fourth fusion (ds10F3, FIG. 5) was obtained from a Ha ds10 G1 genomic DNA fragment between Sal I (−1576) and Pvu II (+1204), purified from ds10G1S6 plasmid (FIG. 1), after digestion with both restriction enzymes. This fragment was ligated with vector pBI101.3 vector, previously digested with Sal I and Sma I. The ds10F3 fusion thus contains the promoter and the same 5'-flanking sequences of Ha ds10 G1 present in ds10F1 fusion, as well as the first exon (From +1 to +145), the total intron (from +146 to +1169) and part of the second exon of Ha ds10 G1 (from +1170 to +1204), fused in phase with the pBI 101.3 GUS gene. In all cases the nucleotide sequence corresponding to the fusion zone, between the GUS and the Ha ds10 G1 sequences, was tested by sequencing reactions with the Sanger (dideoxy) method, using GUS sequences as the primer: 5'-ACGCGCTTTCCCACCAACGCTG-3' [SEQ ID NO: 3].

Figure 6:
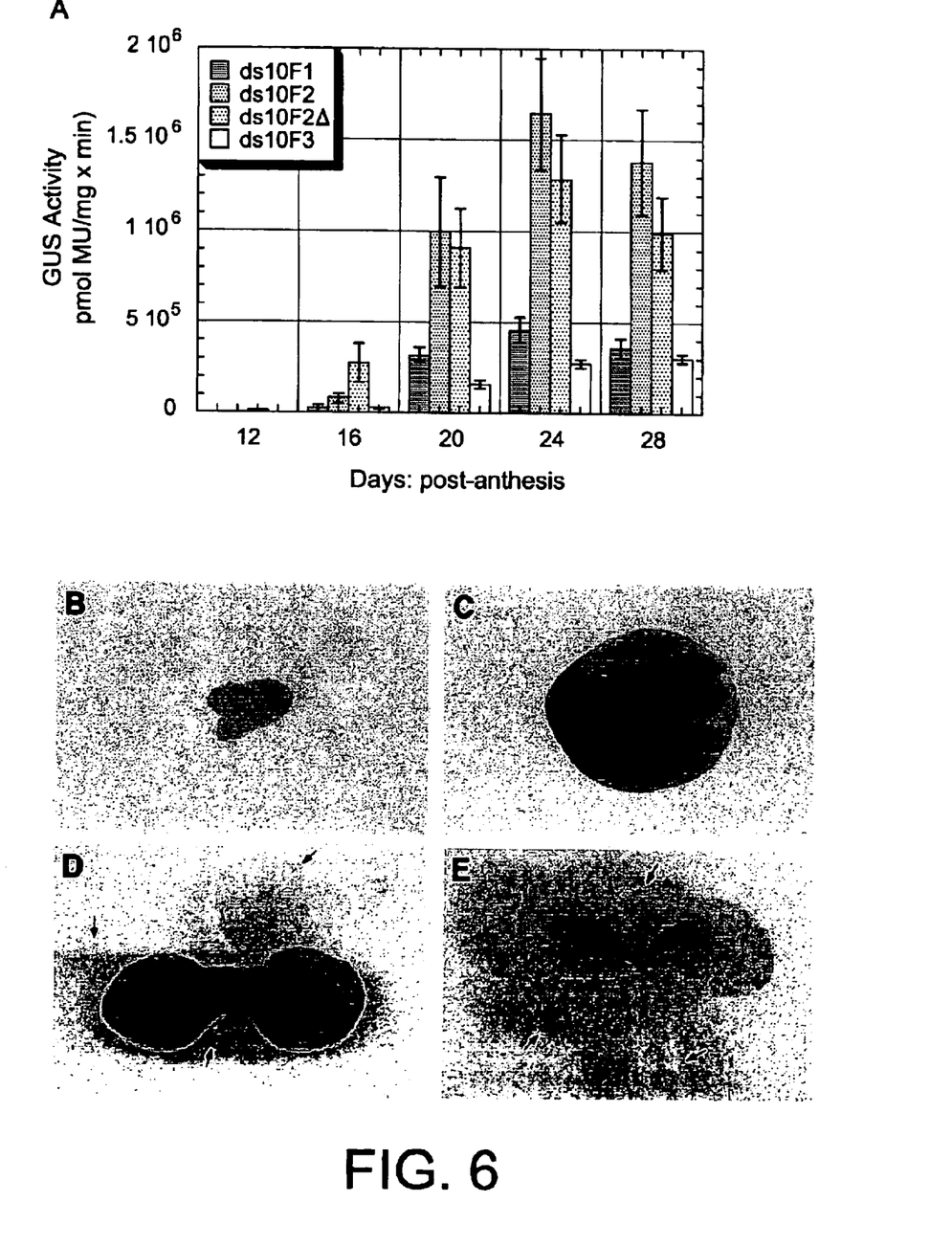

The T-DNA in ds10F1, ds10F2, ds10F2Δ and ds10F3 fusions (FIG. 5) was mobilised from *A. tumefaciens* (LBA 4404), obtaining different tobacco transgenic plants with independent integrations of each chimeric gene. These plants were obtained and characterised by standard techniques as described in detail by Coca M A, Almoguera C, Thomas T L and Jordano J, [in *Plant Molecular Biology*, 31: 863–876, 1996]. The expression of GUS gene was analysed both in developing seeds and under normal growth conditions (without exogenous stress); as in seedling tissues, in the latter case the expression changes induced by ABA and dehydration treatments were studied. The seed analysis were carried out with the original transgenic plants (T0), while for the seed analysis of the seedlings descendants of these plants (T1) were used, which are segregating for the chimeric genes. Quantitative studies by fluorometric analysis of GUS expression levels and their temporal patterns, as well as qualitative studies which analysed histochemically the spatial patterns of expression (tissue specificity) were carried out. These studies were carried out as described in detail by Coca M A, Almoguera C, Thomas T L and Jordano J, [in *Plant Molecular Biology*, 31: 863–876, 1996]. In total, the following number of tobacco transgenic plants, T0 "functional", containing the chimeric genes were obtained and analysed: containing ds10F1: 14 plants, containing ds10F2: 7 plants, containing ds10F2Δ: 8 plants, and containing F3: 23 plants. These plants showed high levels of GUS gene expression in seeds (as a result of the activity of the Ha ds10 G1 gene promoter and regulatory sequences), as illustrated in FIG. 6 (panels A–C). The integration of the different chimeric genes in the DNA of the transgenic plants was characterised by Southern analysis using probes for the coding GUS gene region; PCR amplifications of the sequences close to the ds10::GUS splice, using the 5'-ACGCGCTTTCCCACCAACGCTG-3' [SEQ ID NO: 3] (GUS) and 5'-GAGTGAACAgAATtcCATCACAACAGGG-3' [SEQ ID NO: 4] (ds10Eco RI) primers; or by the Kanamycin resistance segregation test (conferred by the nptII gene), performed as described in Jordano J, Almoguera C, and Thomas T I, *The Plant Cell* 1: 855–866, 1989. These analysis determined that the T0 plant selected for the seed expression studies contained 1 to 5 integrations independent on the corresponding chimeric gene. FIG. 6 illustrates the more relevant results obtained in the study of the expression of the chimeric genes analysed in transgenic plants. These results are described in detail below.

GUS expression during seed maturation under controlled growth conditions (without exogenous stress), was analysed by fluorimetric (FIG. 6A) and histochemical (summary in FIGS. 6B–E) assays. The fluorimetric assays were carried out in seeds at defined maturation stages, 12, 16, 20, 24 and 28 days post-anthesis (dpa). For each T0 plant and maturation stage, two different floral capsule extracts were prepared, and the GUS activity was assayed with Methylumbelliferylglucuronide (MUG) in duplicate (in total four activity determinations per development stage and per individual transgenic plant). The statistical significance of the differences observed with the different GUS fusions was determined, after logarithmic normalisation of the data obtained, by variance analysis [ANOVA, see: Nap I P, Keizer P, and Jansen R, in *Plant Molecular Biology Reporter* 11: 156–164, 1993]. The histochemical assays were carried out with material dissected from seeds, at defined development stages, from the following number of transgenic plants: d10F1, 5, ds10F2, 6, ds10F2Δ, 6 and dsF3, 19. The endosperm and the embryos dissected from individual seeds were stained with X-gluc, for 150 min at 25° C., approximately 150 seeds from each transgenic plant were analysed in this manner.

All chimeric genes produced high levels of GUS expression in seeds, reaching average maximum values of $1.65 \times 10^6$ pmol MU/mg×min (FIG. 6A: at 24 dpa). The histochemical assays confirmed these high activity values, since both the embryos (FIGS. 6B and C) and the endosperm (FIG. 6C) were strongly stained from 12 dpa (FIG. 6B) and with only 150 min of reaction. In both cases fairly homogeneous spatial distributions of the GUS activity were observed (FIGS. 6B–C). Furthermore, these expression patterns do not differ qualitatively between the different chimeric gene transgenic plants (data not shown).

The fluorimetric assays revealed interesting quantitative differences between the different ds10::GUS fusions. These differences depend on the Ha ds10 G1 sequences present in the fusions. In some cases the statistical significance of these differences could be demonstrated (with a confidence level of 95%), which experimentally demonstrates the contribution of the different sequences tested (promoter and 5'-flanking sequences, coding sequences, 3'-flanking and intron) to the embryonic expression patterns observed. The presence of Ha ds10 G1 3'-flanking sequences in the fusions increases the GUS expression levels in seeds between 20 and 28 dpa (compare fusions ds10F2 and ds10F2Δ, with ds10F1 in FIGS. 5 and 6A). This difference is statistically significant (for example at 28 dpa: F=5.397, P: 0.0213), and is caused by the Ha ds10 G1 sequences present in the ds10F2Δ fusion (see FIG. 5); since no significant differences were found between the GUS activity of ds10F2 and ds10F2Δ (for example, also at 28 dpa, F=0.274, P=0.6015; see FIG. 6A). In the case of ds10F2Δ, the stimulating effect of the 3'-flanking sequences also occurs and is highly significant, in earlier embryonic maturation development stages (FIG. 6A, 16 dpa; F=16.607, P=0.001). On the other hand, in these stages (between 12 and 16 dpa) ds10F1 and ds10F2 GUS activities do not differ significantly (e.g. at 16 dpa: F=2.762, P=0.0983; see FIG. 6A). Overall these results show that ds10F2Δ is the constructed and tested fusion that works the best in tobacco seeds from 16dpa; and that this is due to the effect of Ha ds10 G1 3'-flanking sequences included in it. It is not know whether this effect is caused by transcriptional activation, or caused by mRNA stabilisation mechanisms, or by a combination of both. In any case the effect is clear and of potential usefulness to design new chimeric genes with more efficient expression in seeds, since relatively early embryonic maturation stages (see also the section "Other Examples").

On the other hand, the comparison of the GUS activities in plants with the ds10F1 and ds10F3 fusions allowed to investigate the possible effects of the presence of the intron (and/or Ha ds10 G1 coding sequences in which these fusions differ, FIG. 5) on the expression of both fusions. In transgenic tobacco seeds these comparisons demonstrated that the presence of the intron (plus the first total exon and part of the second exon) does not have positive effects on GUS expression, which must therefore be essentially conferred by the Ha ds10 G1 promoter and the sequences present in ds10F1 (FIG. 6A). Thus for example, the activities of ds10F1 and ds10F3 are not statistically different between 12 and 28 dpa, except at 20 dpa (F=4.73, P=0.031) and then the presence of additional sequences in ds10F3 significantly reduced the GUS activity observed. Therefore, even though it is highly probable that the intron is correctly processed in the seeds of heterologous systems such as tobacco (there is not any formal proof), its possible regulatory role in embryonic development is unclear. However other observations do not exclude that the additional Ha ds10 G1 sequences in ds10P3 (including the intron) may have regulatory roles in other tissues (see below the effect of these sequences on residual expression of ds10::GUS fusions in pollen and seedlings).

Embryonic specificity (to seeds) of GUS expression conferred by the Ha ds10 G1 sequences in tobacco transgenic plants was verified through investigations in other tissues; both in the absence of stress as well as after dehydration and ABA treatments. In the case of T0 plants, the only tissue wherein GUS activity was detected by fluorimetric and histochemical assays, was mature pollen. In other tissues the activities detected barely exceeded background levels (non-transformed tobacco plants). For example, in T0 plant leaves of about two months of age: 0–50 pmol MU/mg×min. The activities detected in pollen are marginal (almost three orders of magnitude less) when compared with those of seeds from the same transgenic plants. Furthermore, this expression could be an artefact and depend on the use of GUS gene as an indicator in the fusions [according to Uknes S. Dincher S, Friedrich L, Negrotto D, Williams S, Thompson-Taylor H, Potter S, Ward E, and Ryals J, in the *Plant Cell* 5: 159–169, 1993]. However, it was surprisingly observed that the activity measured in the pollen of the 9 ds10F3 plants was (136±64 pmol MU/mg×min) significantly less than that of the 5 ds10F1 plants (6427±1294 pmol MU/mg×min; F=72.573, P=0.0001). The latter could indicate that, unlike what is observed in seeds during most of their embryonic development (FIG. 6A), the presence of the additional Ha ds10 G1 sequences in ds10F3 (including the intron) may reduce the expression of the chimeric genes containing them in other tissues or stages of development.

The possibility of expression of the ds10::GUS fusions being induced by hormones (ABA) or stress treatments (water deficit) in tobacco transgenic plants (T1) at different times in its vegetative cycle was also checked. In order to do this, descendants of 8 different original plants were selected, after germination in MS medium with 300 μg/ml kanamycin, containing ds10F1, ds10F2Δ and ds10F3; and another 6 with ds10F2. The resistant seedlings were transplanted in MS medium. Various experiments were carried out with seedlings, both at 8 and 15 days after imbibition. For the ABA treatments, the seedlings were transplanted in MS plates supplemented with 100 μM ABA and cultivated in this medium for 4 days at 25° C. in light. The control seedlings were also transplanted in MS medium without ABA. Water stress was induced by placing the seedlings for about 5–6 hours in a laminar flow hood between two filter papers. After the different treatments, the seedlings were processed either individually (for the histochemical assays with X-gluc, by 14 h incubations at 25° C.); or jointly (pool analysis), for the GUS activity fluorimetric assays as described previously. The adult transgenic plant treatments, were carried out using individual plants propagated as vegetative clones obtained from each original plant. To do this, the seedlings selected from each transgenic plant were transplanted to vermiculite imbibed with Hoagland 0.5X medium. From each seedling three complete explants were obtained, which were placed in hydroponic culture, after recovery, in liquid Hoagland medium (0.5×). The experiments were carried out when the plants had completely recovered from the propagation process, and had roots, stem and about 10–12 leaves. Therefore, genetically identical plants from each selected transgenic seedling were used for the different treatments. The ABA treatments were carried out by adding the hormone to the medium (100 $\mu$M) and analysing the GUS activity in the plants after 24 h. Water stress was induced by removing the root from the container with the medium, also analysing the plants 24 h after starting the treatment. The effect of the different treatments was assessed in three independent experiments performed with the following number of T1 plants for each fusion (the number of T0 plants from which they proceed in each case is given in parenthesis): ds10F1, 11 (6); ds10F2, 10 (5); ds10F2$\Delta$, 5 (3); and ds10F3, 10 (5).

The experiments carried out both in seedlings and in adult plants which confirmed the embryonic specificity of the expression conferred by the Ha ds10 G1 sequences to the different fusions, also provided additional clues to the possible regulatory role of the Ha ds10 G1 sequences present in ds10F3 (including the intron) previously mentioned. Thus, both in control adult plants as in treated plants, minimum GUS activities (from 3 to 300 pmol MU/mg×min) were detected in all the tissues analysed (roots, stem, leaves and apical meristem). These activity levels are only slightly above the background levels and can only be detected fluorimetrically (data not shown).

In 8 dpi seedlings, the expression of all the fusions is about two order of magnitudes lower than the maximum levels reached in seeds. This expression rapidly decreases between 8 and 15 dpi (e.g. ds10F1 goes from 2864±182 to 813±104 pmol MU/mg×min); and is exclusively restricted to embryonic tissue (cotyledons), without being detected in other vegetative tissues (radicle, hypocotyl, leaves)—differentiated after germination (FIGS. 6D and E, and data not shown for the other fusions). These results confirm the embryonic specificity of the regulation by Ha ds10 G1 sequences in transgenic tobacco plants. Apart from the general reduction in GUS activity values mentioned previously, differences between the values of the different fusions, some of them statistically significant, were observed. These differences were qualitatively similar to those observed in seeds (FIG. 6A). Among them, and due to their possible applied interest, the reduction of expression after germination, mediated by the Ha ds10 G1 sequences present in ds10F3 (including the intron) is illustrated. This effect is observed as a significant reduction of GUS activity when the ds10F1 and ds10F3 plant expression patterns are compared (FIGS. 6D and E). The statistical analysis of the quantitative ds10F1 and ds10F3 data confirmed the significance of this difference, both at 8 dpi (F=4.36, P=0.04) and at 15 dpi (F=4.39, P=0.039). Additionally, a moderate induction of GUS by ABA treatment in ds10F1 seedlings was observed, which is statistically significant (from 2864±182 to 5790±733 pmol MU/mg×min; F=5.413, P=0.023). In the case of ds10F3 there was no significant induction by the same treatment (from 1502±195 to 2338±211 pmol MU/mg×min; F=2.58, P=0.11). The different treatments did not substantially affect the tissue specificity, or the order of magnitude of the expression observed for the different ds10::GUS fusions (data not shown).

Other Examples

Other chimeric genes can be obtained, in an analogous manner to that of the one described in detail in the previous example, said chimeric genes containing 5'-flanking, and(or) 3'-flanking (terminators), and(or) coding sequences from Ha ds10 G1, combined with sequences from other genes. These examples do not involve any additional technical complications to those described in more detail in the previous sections, for which reason they can easily be carried out by persons with sufficient knowledge in the field of the invention technique. Thus for example, in ds10::GUS fusions the Ha ds10 G1 could have included other longer 5'-flanking (FIG. 1) sequences of the same gene to increase its expression level in seeds as described in Coca M A, Almoguera C, Thomas T L, and Jordano J, in *Plant Molecular Biology*, 31: 863–876, 1996. Equally, the GUS sequences could be substituted by others, coding for different proteins or peptides (natural or artificial), whose regulated production in plant seeds could be of industrial interest. Examples of these last possibilities, non exclusively, would be the fusion with Ha ds10 G1 sequences of coding sequences of genes involved in fatty acid biosynthesis in seeds [Voelker T A, Worrell A C, Anderson L, Bleibaum 3, Fan C, Hawkins D J, Radke S E and Davies H M, in *Science*, 257:72–74, 1992], of storage proteins with compositions rich in specific amino acids [Saalbach I, Pickardt T, Machemehl F, Saalbach G, Schieder O, and Muntz K, in *Molecular and General Genetics* 242: 226–236, 1994], or peptides with antigenic or pharmacological activities [Vandekerckhove J, Van Damme J, Van Lijsebettens M, Botterman J, De Block M, Vandewiele M, De Clercq, Leemans J Van Montagu, M and Krebbers E, in *BioTechnology* 7: 929–932, 1989]. These fusions would be carried out and used in an analogous manner to what is described in the publications cited as an example (not exclusive) in each case. To facilitate these possibilities, a plasmid (ds10EC1) was created, that contains an expression cassette including the promoter and the 5'- and 3'-flanking sequences of Ha ds10 G1 present in ds10F2$\Delta$ (see FIG. 5). Between both sequences and through directed mutagenesis [Chen E and Przybila A E, in *BioTechniques* 17: 657–659, 1994] an Eco RI restriction site was added. The addition of said restriction site allows the insertion of gene sequences, or of the corresponding peptide sequences, as previously mentioned (available in other laboratories, or that could be designed or synthesised). The ds10EC1 plasmid was constructed from ds10G1S3$\Delta$10.5 (FIG. 1). From this plasmid, the Ha ds10 G1 sequences between positions −1574 (Sal I) and +98 by PCR were amplified, by using DNA polymerase Pfu and the primers 5'-ATTAACCCTCACTAAAG-3' [SEQ ID NO: 5] (T3) and 5'-GAGTGAACAgAATtcCATCACAACAGGG-3' [SEQ ID NO: 4] (ds10Eco RI). In the latter the three sequence changes (indicated in lower case letters) introduce the new Eco RI site in the position of the initiation codon. After PCR, a 199 pb (megaprimer) DNA fragment is purified, which along with the 5'-AATACGACTCACTATAG-3' [SEQ ID NO: 6] (T7) primer is used for a second PCR amplification of ds10G1S3$\Delta$10.5. The amplified DNA (795 pb) was digested with Eco RI and Sph I. The resulting DNA fragment (125 pb), with the Ha ds10 G1 sequences between Sph I (−126) and the new Eco RI site, was purified and ligated by replacing in ds10G1S3 the Ha ds10 G1 (FIG. 1) sequences between positions −126 (Sph I) and 1086 (Eco RI). After this step, the PCR amplified sequence was verified by means of sequencing (Sanger's method) using the T3 primer. Finally, an Ha ds10 G1 genomic DNA fragment (FIG. 1) was inserted in the plasmid obtained in the previous step, with sequences between +1086 (Eco RI) and ≈+3000 (Xba 1), obtaining the ds10EC1 cassette (FIG. 4), cloned in the pBluescript SK+plasmid. The 3' end of ds10EC1 DNA differs from that of ds10F2Δ only by 119 additional nucleotides, corresponding to the intron and second exon sequences of Ha ds10 G1. Furthermore, the Ha ds10 G1 sequences in ds10EC1 differ from the corresponding ones in ds10F2Δ in the absence of nucleotides 1–98 of the first exon (FIG. 5).

Given that the presence of additional Ha ds10 G1 sequences in ds10F3 (including the intron, the first exon and part of the second exon) reduced the expression of this chimeric gene specifically in non embryonic tissues (Example 3, FIGS. 6D–E), it is conceivable that such sequences may be used to confer seed specificity to other chimeric genes with different promoters. The design of such chimeric genes does not involve additional technical difficulties other than those described in the previous sections: see for example the detailed procedures on the use of plant introns to prevent the expression of chimeric genes in Agrobacierium [Mankin S L, Allen G C and Thompson W F. *Plant Molecular Biology Reporter* 15: 186–196, 1997].

The chimeric genes containing the Ha ds10 G1 regulatory sequences could be transformed to other plants different from tobacco (the model system used in example 3). Among these, there are plants with major economical interest such as: sunflower, soybean, oilseed rape, "canola", maize, wheat, barley, rice, cassava, bean, peanuts, etc. whose genetic transformation is possible and has been sufficiently documented in the scientific literature: see for example lindsey K, Ed. (1993). [*Plant Tissue Culture Manual*. Kluwer Academic Publishers]; and the review by Christou [*Trends in Plant Science*. 1: 423–431, 1996]. The results shown in example 3 demonstrate that, in tobacco, the genes constructed with the Ha ds10 G1 regulatory sequences have a high activity since relatively early embryonic maturation stages, and also maintain the seed specificity characteristic of Ha ds10 G1 in sunflower. These results could also be obtained with other plants, such as those previously mentioned.

Description of the Figures

FIG. 1. Upper section: restriction map of the Ha ds10 G1 genomic sequences that flank its coding region. The continuous lines on the map indicate the different genomic DNA fragments subcloned in pBluescript SK+ vector (the names of the respective fragments are indicated over each fragment). The plasmids prepared by Exo III deletions are indicated over the original plasmid (ds10G1S3ΔSacI), indicating in each case the deletion end. On the lower section of the figure a detailed restriction map of the region whose nucleotide sequence was determined, is shown. The extension of the different reactions used to assemble the different sequences of both DNA strands, are indicated by horizontal arrows (above the map for the coding strand, and underneath the map for the non-coding strand). The transcription initiations sites are indicated with arrows. Scale bars are included for both maps.

FIG. 2. Functional implications of the RY1 (−129) sequences in the trans-activation of the Ha ds10 G1 promoter. Transient expression experiments carried out after bombarding the sunflower embryos with DNA coated microprojectiles. The results of 5 independent experiments, in which the different plasmid mixtures (described in Example 1) where bombarded five times in each experiment, are presented. The average β-glucuronidase (GUS) activities normalised versus luciferase activity (LUC), as well as the standard error (indicated with bars), are presented. Key: F2, pSKds10F2; F2ΔRY1, pSKds10F2ΔRY1; ABI3, samples with the effector plasmid. A significant decrease in the relative GUS/LUC activity is observed, due to a mutation in the RY1 box. The basal activities for pSKds10F1 (without including the effector plasmid) are of the order of 46±8.

FIG. 3. Accumulation patterns of Ha ds10 G1 gene mRNA in sunflower. The autoradiograph shown corresponds to the RNAse A protection tests, after hybridising a gene riboprobe with different total RNA samples. An accumulation of messenger RNA produced from Ha ds10 G1 transcription initiation sites (as protected fragments indicated by the numbered arrows) is observed. These fragments are only detected in embryos (Emb) from 10 to 20 dpa and in mature seeds (25 dpa), but not in other samples tested, such as seedlings (Germ) or seedlings treated with ABA (Germ+ABA). The carrier tRNA corresponds to control hybridisations with yeast tRNA. The bands corresponding to the mRNAs produced from the different initiation sites are indicated with numbers and arrows. The initiation site number 3 (indicated in parenthesis) has not been experimentally confirmed by primer extension. On the left margin are included molecular size markers (pBR322/Hpa III).

FIG. 4. Localisation of mRNA in sunflower embryos sections at 12 (A and B), 21 (C–E), and 28 dpa (F–H). The following riboprobes were used in each case: ds10 (−), A, C, F, H; ds10 (+),E, and 18S rRNA, B, D, G. Scale bar=500 μm (Except in F, 125 μm). Palisade parenchyma=pp. The arrows mark the procambium.

FIG. 6. Expression of ds10::GUS fusions in tobacco transgenic plant seeds. Panel A: Summary of quantitative data (fluorimetric determinations). The average of GUS activities in transgenic plant seeds (TO), and its evolution through the different embryonic development stages is shown. The data corresponding to each fusion are indicated by the symbols in the upper left-hand insert. The bars indicate the standard errors. Panels B–E: representative selection with results of the histochemical GUS activity localisation experiments: B. embryos at 12 dpa (plants ds10F2Δ, T0). C. embryos and endosperm at 16 dpa (ds10F2Δ plants, T0). D. seedlings at 15 dpi under control conditions (ds10F1 plants, T1) E. seedlings at 15 dpi under control conditions (ds10F3 plants, T1) In panels D and E, the arrows indicate the plant tissue without GUS activity (leaves and hypocotyl).

List of Sequences

SEQ No. 1: Ha ds10 G1 gene nucleotide sequence. The transcription initiation sites experimentally determined (site 3, which has not been confirmed by primer extension is indicated in parenthesis) are indicated by arrows. The coding zone is shown by its amino acid translation indicated by the letter (L01 etc.) code underneath the nucleotide sequence. The termination codon is indicated by an asterisk. The sequence is numbered (on the left margin) starting from the initiation codon. The intron sequences are shown in lower case letters. The TATA box (in position −86) and RY box (−129 and −65) mentioned in the text (Example 1) are shown underlined.

What is claimed is:

1. An isolated nucleic acid molecule having seed specific promoter activity selected from the group consisting of
    a) an Ha ds10 G1 gene 5' flanking sequence comprising nucleotides 1–1576 of SEQ ID NO:1 or
    b) fragments of the Ha ds10 G1 gene 5' flanking sequence comprising nucleotides 1–1576 of SEQ ID NO:1, said fragments having seed specific promoter activity.

2. An expression cassette comprising the isolated nucleic acid molecule of claim 1, and a transgene.

3. The expression cassette of claim 2, further comprising the Ha ds10 G1 gene 3' flanking sequence, wherein said 3' flanking sequence comprises nucleotides 2879–3617 of SEQ ID NO:1, or a fragment thereof.

4. The expression cassette of claim 2, selected from the group consisting of ds10F1, ds10F2, ds102D, ds10F3 and ds10EC1.

5. A vector comprising the expression cassette of claim 2.

6. A host cell comprising the vector of claim 5.

7. A transgenic plant transformed by the expression cassette of claim 2.

8. The transgenic plant of claim 7, selected from the group consisting of sunflower, tobacco, soya, oilseed, rape, canola, maize, wheat, barley, rice, bean, cassava and peanut.

9. A method for expressing a transgene in seeds, seed parts, seed extracts, seed embryos and seedling tissues, said method comprising transforming a plant with the expression cassette of claim 2.

10. A method for producing a substance resulting from expression of a transgene, said method comprising transforming a plant with the expression cassette of claim 2.

11. The method of claim 10 wherein said substance is selected from the group consisting of proteins, bioactive substances and oils.

12. A method for expressing a transgene in seed, seed parts, seed extract, seed embryos and seedling tissues, said method comprising transforming a plant with the vector of claim 5.

13. A transgenic plant transformed by the vector of claim 5.

14. The transgenic plant of claim 13, selected from the group consisting of sunflower, tobacco, soya, oilseed rape, canola, maize, wheat, barley, rice, bean, cassava and peanut.

15. A method for producing a substance resulting from expression of a transgene, said method comprising transforming a plant with the vector of claim 5.

16. The method of claim 15, wherein said substance is selected from the group consisting of proteins, bioactive substances and oils.

* * * * *

SEQUENCE LISTING

<160> NUMBER OF SEQ ID NOS: 6

<210> SEQ ID NO 1
<211> LENGTH: 3617
<212> TYPE: DNA
<213> ORGANISM: Helianthus annuus
<220> FEATURE:
<221> NAME/KEY: exon
<222> LOCATION: (1577)...(1721)
<220> FEATURE:
<221> NAME/KEY: exon
<222> LOCATION: (2746)...(2879)
<220> FEATURE:
<221> NAME/KEY: intron
<222> LOCATION: (1722)...(2745)
<220> FEATURE:
<221> NAME/KEY: misc_feature
<222> LOCATION: (1448)...(1455)
<223> OTHER INFORMATION: RY box
<220> FEATURE:
<221> NAME/KEY: misc_feature
<222> LOCATION: (1512)...(1519)
<223> OTHER INFORMATION: RY box
<220> FEATURE:
<221> NAME/KEY: polyA_signal
<222> LOCATION: (3139)...(3144)
<220> FEATURE:
<221> NAME/KEY: polyA_signal
<222> LOCATION: (3220)...(3225)

<400> SEQUENCE: 1

| | | | | | |
|---|---|---|---|---|---|
| gtcgacttct | tcatcttcgt | ctaagtgttg | agtatcgagt | acaaattatt | catcttcgtt | 60 |
| gtcatcgtat | atgagaagca | tgtgtttaac | attatctctt | ggatattgag | acggtggact | 120 |
| ccgataagca | aacgggtcaa | aagcgttttg | ggcttccgta | ggatactcgt | acacacccgg | 180 |
| tgcaaccatc | gtgggacttt | gtggtaatga | aaaaaactgt | ggtggatagt | tgggttgggg | 240 |
| ttgggtgttg | taaaaacccg | tttgtggaaa | aaatgtggtg | ggaagttggg | ttggtacaca | 300 |
| atagatccac | ctcgtctact | ttgcgagccg | cgcccctcg | cattcgaacc | ggaatccgat | 360 |
| acttttttc | ttttcatgac | ccttgttttg | tctatccatg | gtatgcatct | gaattggtaa | 420 |
| attgggtgaa | aaatggaatg | tttaacatgg | taaaatggaa | tgttataatt | ataaaggtat | 480 |
| ttaatgtttt | ttttaaacc | ataaacggtc | atatagccgt | ttaaagcaca | acggtcaagt | 540 |
| ccccaacggt | caaatcaagc | caaacaatca | agtcccgcat | gtggcatata | tcccctgctt | 600 |
| tgaaccaggg | ccggcccaag | cctaagaatt | ttgaggcttg | ggctttaggc | ctctaaatca | 660 |
| atagggactc | taacttaaaa | aaattatata | tgatatttag | gttaagttga | atttatcttt | 720 |
| atatgtacaa | aaaatatat | ataattccaa | aataaaaaat | aaaaaataa | attaacttcg | 780 |
| ccaacaataa | atcttttgtt | atgttttgcc | ttttgttttt | ttaaaaaag | gctcaaattt | 840 |
| ttaatttgct | ttaggccacc | aaaatggtta | aaccgacctt | gctttgaacc | atacccacac | 900 |
| gacaaattag | gggatacgga | gtggggtcg | gcaaaccaat | gccataaaac | tttgccgatc | 960 |
| aaagtttcac | catttcggtg | attgtttgcc | gatgcggcga | ggaggaagaa | gagagaggag | 1020 |
| ggtagtgtga | ggtggggtcc | attccaatct | caactaatca | catttttttc | ctttttttta | 1080 |
| tttaaaaagt | ttaccacttc | actaaatgtc | taaaccattg | ccaacacttt | tcaccaaagt | 1140 |
| ttaaacattt | ttctctgatt | gacgtggcac | actctcattg | gttgatttt | tagtttgcca | 1200 |
| ctctcaattg | tttaaccact | ccttacaccc | tcttatgtga | gcggtggtgt | tcccaagcg | 1260 |
| acaaagggc | ttaccgcaac | cccttaccgc | ttccaacctt | tacacccta | tcttctgcct | 1320 |

```
atactgcatg tcactctatt gcagactatc tgagatagct acaacctaac gacttaaggt    1380
gaggacacgt gtatctccaa aacccacttc gtcaccctta ccaccacgtc atcataccac    1440
gtgccaacat gcatgctagt atcttctcta ctatacacat acttatgtac tatatatatt    1500
caccaaaatt acatgcatgt tagcaccctc aattgtacaa cacaacttaa caacttaagt    1560
taaaagagtg aacaaaatgg catcacaaca gggacaacaa acacgcaaaa ttccggaaca    1620
ggagaagaag gatctcgacc aacgagcagc taaaggcgag accgttgttc cgggtggtac    1680
tcgtggcaaa tctcttgagg ctcaagaacg tcttgctgaa ggtatatgct tatttagtta    1740
aatttacata cgtattgggg atggccgttt gatatttagc aaacggcaac ccgaatattt    1800
aggggcccat gatttgacat acatatttga ataagattaa ggggcctaga ggtgtacaaa    1860
tcccttaaa aaagggtccg gttttaaccg dacggaaatg gtttctaaaa tagcggttcg    1920
gttttttaact ggttttacat ggtgggcagt cgaactggta ctagtagatt cggtaagcga    1980
tttgggacaa aaaacgtttt tttaactggt tttgaagatc agtaatacta accggtatgc    2040
aaactgccag ttcgggttga aactggtttc ttttctttt tcaaaaaaga acggtatgg    2100
gacaaaaaac gttttttaa actggttttg aagatcaata atactaaccg gtatgcaaac    2160
cgccagttcg gttcgggtta aaactggttt ttttttttt tttaagaag cggtaaaaaa    2220
accggtttcg gtcataaacc gattttttta acacctacaa gggggccatg atttaaaaaa    2280
aaagcggtaa aaaaaaccg gtttcggtca taaaccgatt ttttaacac ctacaagggg    2340
gccatgattt aagatgaagt atcggagctc gtgatttaac ataaagtacc tcaaacggcc    2400
gcagtttgat tcaagcgcaa acccgtcgtt ctacgactag tggcgaagct tgagatctcc    2460
gattgggggt cgaaaacgtt tatcccaaa aattctata gaacggggt cgaaaacgtg    2520
tatactcaaa aaattctata cgaaagctac ataccgagc gaaaagttcg ggtctggcac    2580
acaccccctc cccctcttc taacctacgc ccctagctat gacggtgtgg gtagagtcca    2640
ccctttcagt agctttttttg cgaattcaca ttagtttatt ttatagttgt agtgatgcat    2700
aataatatat gcatgtactt aattttgtgt ttggtggtgg tgaagggcgg agcaagggag    2760
gacaaacgag gaaagaccag ctgggaactg aagggtacaa ggagatgggg aaaaagggcg    2820
gtcagaccac cggtgacaag tcggctggtg agcgagagga ggaggaggag gaggactaga    2880
tagtcaatag tggtgtgatg gtgtttgcat gtacgatgat gttaatttcc atgtttata    2940
tatgtgtatg tacctgtagt atggtttagc tcgtgtttca tgttttgttg gtcgttttgg    3000
tatcttcttt agtgcatgta cgactagtag tcctatgatg atgtgatgtg atttgcatat    3060
gttgatataa tggtaagtac aagttttatc tatctatctt ttctttcggc tagagtttac    3120
aaaatgtgta cggatgacaa taataagcaa cttatatttt tccatacaag cttattatgt    3180
gactattgcc caataaggca ataagtaagt gagccaataa ataatagccg gttatgctgt    3240
aacaactatt gtgacaacaa tattcttta ccgaataaat aaaaataagt aagtattagg    3300
agccaataaa taaataaccg gttaatgag aaaagcacca aaatagcctc tttgatcaat    3360
agaattatga aaatagtctc gactcgacct ttttgaataa cccttcatct cctgtgttgc    3420
gcgatcttcg cccggacgac acgtgtctag tgaacatgcc tattctgatt agtggtgcac    3480
aaatcggggtt ttttttaaa aaacgggttt cgggtaggat cgggtttttt taaaaccggg    3540
tcgggtccgg gtcgggttttt ctaccaaaaa tgtataccct gtataccggg ttcgggtcgg    3600
gttttataaa acccggg                                                  3617
```

-continued

```
<210> SEQ ID NO 2
<211> LENGTH: 24
<212> TYPE: DNA
<213> ORGANISM: Artificial Sequence
<220> FEATURE:
<223> OTHER INFORMATION: Synthetic Primer

<400> SEQUENCE: 2
ctcctgttcc ggaattttgc gtgt                                          24

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
acgcgctttc ccaccaacgc tg                                            22

<210> SEQ ID NO 4
<211> LENGTH: 28
<212> TYPE: DNA
<213> ORGANISM: Artificial Sequence
<220> FEATURE:
<223> OTHER INFORMATION: Synthetic Primer

<400> SEQUENCE: 4
gagtgaacag aattccatca caacaggg                                      28

<210> SEQ ID NO 5
<211> LENGTH: 17
<212> TYPE: DNA
<213> ORGANISM: Artificial Sequence
<220> FEATURE:
<223> OTHER INFORMATION: Synthetic Primer

<400> SEQUENCE: 5
attaaccctc actaaag                                                  17

<210> SEQ ID NO 6
<211> LENGTH: 17
<212> TYPE: DNA
<213> ORGANISM: Artificial Sequence
<220> FEATURE:
<223> OTHER INFORMATION: Synthetic Primer

<400> SEQUENCE: 6
aatacgactc actatag                                                  17
```